US009402787B2

(12) United States Patent
Brem et al.

(10) Patent No.: US 9,402,787 B2
(45) Date of Patent: Aug. 2, 2016

(54) DEVICE FOR REMOVING A FLUID FROM A VIAL

(75) Inventors: William Brem, Muri (CH); Ralph Egon Kayser, Luzern (CH); Andy Greter, Baar (CH)

(73) Assignee: MEDMIX SYSTEMS AG, Rotkreuz (CH)

( * ) Notice: Subject to any disclaimer, the term of this patent is extended or adjusted under 35 U.S.C. 154(b) by 109 days.

(21) Appl. No.: 13/576,352

(22) PCT Filed: Aug. 24, 2010

(86) PCT No.: PCT/CH2010/000206
§ 371 (c)(1),
(2), (4) Date: Jul. 31, 2012

(87) PCT Pub. No.: WO2011/091542
PCT Pub. Date: Aug. 4, 2011

(65) Prior Publication Data

US 2012/0302986 A1 Nov. 29, 2012

(30) Foreign Application Priority Data

Feb. 1, 2010 (CH) ........................................ 115/10

(51) Int. Cl.
*A61M 5/32* (2006.01)
*A61J 1/20* (2006.01)
*A61M 5/00* (2006.01)

(52) U.S. Cl.
CPC ................ *A61J 1/2096* (2013.01); *A61J 1/201* (2015.05); *A61J 1/2013* (2015.05); *A61J 1/2051* (2015.05); *A61J 1/2055* (2015.05); *A61J 1/2058* (2015.05); *A61J 1/2089* (2013.01); *A61J 2001/2013* (2013.01); *A61J 2001/2065* (2013.01)

(58) Field of Classification Search
CPC .................. A61J 1/2096; A61J 1/2089; A61J 2001/2013; A61J 2001/2065
USPC ......................................... 604/181, 411, 414
See application file for complete search history.

(56) References Cited

U.S. PATENT DOCUMENTS 5,037,390 A * 8/1991 Raines et al. ................... 604/83
5,226,900 A * 7/1993 Bancsi et al. ................. 604/411

(Continued)

FOREIGN PATENT DOCUMENTS

DE 35 03 460 A1 9/1985
DE 10 2006 031 712 B3 12/2007

(Continued)

*Primary Examiner* — Tatyana Zalukaeva
*Assistant Examiner* — Andrew J Mensh
(74) *Attorney, Agent, or Firm* — Sughrue Mion, PLLC

(57) ABSTRACT

The invention relates to a device for removing a fluid from at least one container (300), from a vial for example, said container being closed by a closure (320) that can be punctured. The device comprises a base body (271) with a container receiving portion (272) and a hollow needle-like puncturing organ (277) in order to puncture the closure (320) of the container (300) in a removal position of the container (300). The aim of the invention is to enable mounting the container on the device without unintentionally puncturing the closure. This is achieved in that detent structures (274, 275) are provided which retain the container (300) on the device in a removal position and in a mounting position which is different from said removal position. Such a device can be used in particular to fill an applicator (280) with one or more fluid reservoirs from one or more vitals.

14 Claims, 6 Drawing Sheets

(56) References Cited

U.S. PATENT DOCUMENTS

| | | | | |
|---|---|---|---|---|
| 5,304,165 | A | 4/1994 | Haber et al. | |
| 6,258,078 | B1 | 7/2001 | Thilly | |
| 6,358,236 | B1 | 3/2002 | DeFoggi et al. | |
| 6,488,650 | B1 | 12/2002 | Epstein et al. | |
| 6,610,033 | B1 | 8/2003 | Melanson et al. | |
| 7,758,560 | B2 * | 7/2010 | Connell et al. | 604/414 |
| 2002/0079285 | A1 | 6/2002 | Jansen et al. | |
| 2004/0249235 | A1 | 12/2004 | Connell et al. | |
| 2006/0259004 | A1 * | 11/2006 | Connell et al. | 604/403 |
| 2008/0015496 | A1 * | 1/2008 | Hamedi-Sangsari | A61J 1/2089 604/87 |

FOREIGN PATENT DOCUMENTS

| | | | |
|---|---|---|---|
| EP | 0 335 378 | A2 | 10/1989 |
| WO | 88/01881 | A1 | 3/1988 |
| WO | 92/15346 | A2 | 9/1992 |
| WO | 99/17833 | A1 | 4/1999 |
| WO | WO 2008006439 | A1 * | 1/2008 |
| WO | 2009/144085 | A2 | 12/2009 |

* cited by examiner

DEVICE FOR REMOVING A FLUID FROM A VIAL

CROSS REFERENCE TO RELATED APPLICATIONS

This application is a National Stage of International Application No. PCT/CH2010/000206 filed Aug. 24, 2010, claiming priority based on Switzerland Patent Application No. 00115/10 filed Feb. 1, 2010, the contents of all of which are incorporated herein by reference in their entirety.

TECHNICAL FIELD

The present invention relates to a device for removing a fluid from at least one container, closed by means of a seal that can be punctured, e.g. a vial with a septum seal. In particular the invention relates to a device for filling an applicator with at least one fluid reservoir from one or more vials.

PRIOR ART

Particularly in medicine, but also in other technical fields, applicators such as syringes are often used to discharge and apply flowable substances in a controlled and dosed manner. The substances can for example be medicinal products or adhesives for medical or technical applications. A conventional syringe usually has at least one reservoir which holds a flowable substance. This substance is discharged through a distal outlet by means of plunger pushed into an open, proximal end of the reservoir. For subcutaneous or intravenous administration to a patient, for example, these syringes can have an injection needle which is in fluidic connection with the distal outlet.

However, it is often problematical to store flowable substances for a longer period in plastic applicators, as on the one hand the substances can chemically react with the plastic, and on the other hand there is a risk that gas, in particular oxygen from the air, can diffuse though the walls of the applicator or through seals and chemically modify the content. This applies in particular to applications in the field of medicine where chemical purity is of special relevance.

It is therefore known to store the substance to be applied separately in a so-called vial, more particularly a glass vial with a septum seal, i.e. in a sterilisable glass bottle which is sealed at one end with a self-sealing membrane (a septum seal) that can be punctured in order to remove the components to be mixed from the vial only shortly before application into the reservoir. For filling a syringe the septum can be directly punctured with the injection needle of the syringe and the substance stored in the vial drawn up into the syringe. However, as the injection needle poses a potential risk of injury to the user and as sterility of the injection needle must be maintained during administration, any manipulations with the injection needle before the actual administration should be avoided. Furthermore, many pharmaceutical products are known which are stored and sold in lyophilised form, for example as powder, and have to be dissolved in water before being used. The lyophilisates are normally stored in a container sealed with a septum into which water has to be injected before use. This injection can take place mechanically or manually, again by means of a syringe for example. All manner of prior-art devices are conceivable for this.

For this reason adapter-like devices are proposed in the prior art which serve to puncture the septum of a vial and then fill an applicator.

In U.S. Pat. No. 6,358,236 a device of this type is disclosed which has a puncturing element for puncturing the septum of a vial when the device is placed on the vial. The device also has a connector to which a syringe can be attached. The substance stored in the vial can be drawn up into the syringe through a channel extending through the connector and the puncturing element. However the simultaneous mounting of the device on the vial and puncturing of the septum can lead to incorrect manipulations, more particularly unintentional spilling of the fluid contained in the vial.

However, in the prior art there are also devices for removing a substance from a vial sealed with a septum which are designed as filling systems for the simultaneous filling of two reservoirs from two or more vials. These filling systems are used, for example, when two components of a medicinal product have to be mixed with each other prior to application, but cannot be stored in the mixed state. The filling systems disclosed in U.S. Pat. Nos. 6,610,933, 6,488,650, WO 99/17833 and WO 2009/144085 each have at least on puncturing element for puncturing the septum of a vial.

In most device for removing a substance from a vial sealed with a septum the vial is simple pressed into the device in order to puncture the septum. In some of these devices, after being completely inserted into the device and after puncturing of the septum, the vial is fixed to the device by means of a snap connection. However, known devices are not generally suitable for storing the vial directly on the device as accidental puncturing of the septum of a vial cannot be ruled out during transportation or when being handled.

US 2002/0079285 describes a device which can be mounted on a vial before puncturing the septum. During the subsequent screwing of a syringe onto the device, a moveably arranged puncturing element is moved towards the septum in such a way that it punctures it and creates a fluid connection between the vial and the reservoir of the syringe. The device shown in U.S. Pat. No. 6,258,078 is also designed so that the septum can only be punctured when the device is correctly mounted on the vial. By turning a lid which is in threaded connection with the puncturing element the puncturing element is moved towards the vial and the septum is punctured. However, these devices have a relatively complex, multiple-part, structure and are therefore costly to manufacture.

SUMMARY OF THE INVENTION

The present invention provides an adapter-like device for removing a fluid from at least one container sealed with a closure that can be punctured which allows the container to be stored on the device without unintentionally opening the container.

A device for removing a fluid from at least one container, more particularly a vial, sealed with a closure that can be punctured is disclosed which comprises:

- a basic body in which at least one inlet opening and at least one outlet opening are formed which are connected by a fluid channel;
- at least one hollow needle like puncturing element connected to the inlet opening for puncturing the closure of the container, more particularly a septum seal, in a removal position of the container; and
- at least one container holder connected to the basic body for holding the container on the device.

In order to securely hold the container on the device before puncturing of the closure and to prevent unintentional puncturing, the holding device has a first catch structure for fixing the container in a storage position, in which the container is further away from the basic body than in the removal position (and in which the closure has not yet been punctured), by means of releasable snap connection.

Preferably the container is also fixed in the removal position and for this the container holder also has a second catch structure for fixing the container in the removal position on the container holder by means of a snap connection.

The catch structures can interact directly or indirectly with the container. For example, the container can be inserted directly into the container holder, whereby the catch structures directly engage in a corresponding retention structure, e.g. a tapered section, of the container, or the container can be held on a separate mount which can be pushed into or onto the container holder, whereby the catch structures of the container holder interact with the corresponding retention structure of the mount. It is also conceivable that the container holder only has one single catch structure, while the container or the mount has two retention structures, whereby in the storage position the first of these retention structures interacts with the (single) catch structure, while in the removal position the second of the retention structures interacts with the catch structure.

Each of the catch structures is preferably designed as follows: the container holder has a preferably at least partially cylindrical jacket wall. The first catch structure and the second catch structure each have a spring arm formed in the jacket wall, at the free end of which a catch lug is formed extending into the interior of the jacket wall. This allows very simple and cost-effective production. The catch structures are preferably offset, more particularly offset by approx. 180° with regard to the circumferential direction of the jacket wall, i.e. they are diametrically opposite each other in order to take up as little space as possible with as great stability of the container holder as possible. However, in relation to the circumferential direction of the jacket wall, the first catch structure and the second catch structure can be arranged directly next to each other. In the circumferential direction the two catch structure are then only separated from each other with an air gap. Preferably the catch lugs each have an oblique surface, the surface normal of which on the one hand points in the opposite direction to the direction of insertion of the container into the container holder, and on the other hand is inclined towards a longitudinal axis defined by the jacket wall.

Specifically the container holder can be constructed as follows: it has base from which a peg extends into the inlet opening of the basic body. Through the peg and the base there is a through opening, and the puncturing element is held in the through opening.

The device can be used more particularly as a filling device or adapter for filling at least one reservoir of an applicator from at least one container, more particularly a vial. The applicator can be a syringe-like applicator in which the reservoir is defined by a movable plunger, so that the reservoir can be filled by retracting the plunger from a distal end position in a proximal direction. For this, the device preferably has an applicator connector for connecting the reservoir of the applicator with the outlet opening. The applicator connector can be equipped with a holding device, more particularly a releasable snap connection, for the applicator. It can be produced in one piece with the basic body or separately from it. Preferably the applicator connector is, for example, formed by a female Luer cone. It can however also have a special design in which the dead volume is less than in a normal standardised Luer connection.

More particularly the device can be designed for the simultaneous removal of fluids from at least two containers. For this the above features are each at least doubly present. The device then has two or more puncturing elements and just as many container holders for holding two or more containers on the device, wherein each of these container holders has a first catch structure, preferably also a second catch structure. The catch structures can be designed so that they simultaneously fix two or more containers in the storage position and/or in the removal position.

The basic body, the container holder and the applicator connector are preferably made of a thermoplastic material in an injection moulding process.

BRIEF DESCRIPTION OF THE DRAWINGS

Preferred embodiments of the invention will be described below with the reference to the drawings which are only explanatory and should not be interpreted as limiting. In the drawings.

DESCRIPTION OF PREFERRED EMBODIMENTS

In FIGS. 1 to 5 a filling device 200 which is not in accordance with the invention is illustrated, the container holder of which is designed in a conventional manner to remove fluid substances from two containers sealed with a closure that can be punctured. The filling device 200 has a basic body 210 which is of an elongated, essentially disk-shaped form. Formed on the basic body 210 is a central, cylindrical thickening 211, to which the two halves of a flat carrier plate 212 are connected. With its cylindrical axis the thickening 211 defines a longitudinal direction.

Figure 1:
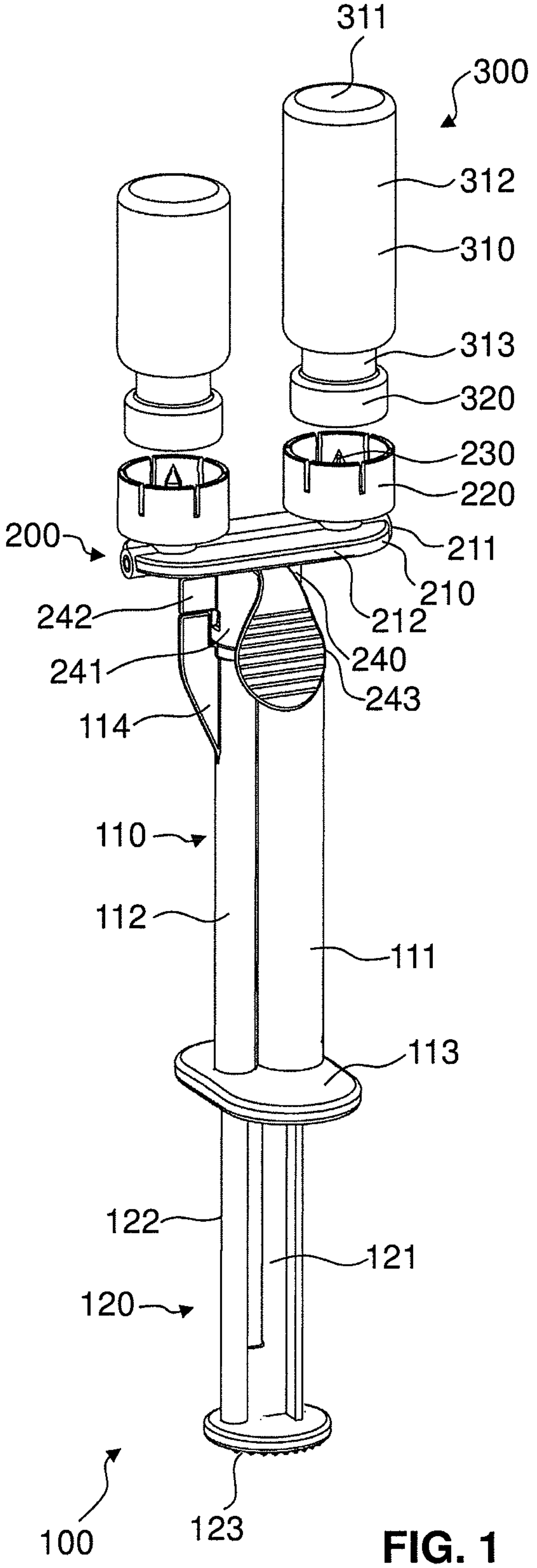
FIG. 1 shows a perspective view of a filling device, the container holder of which is designed in a conventional manner.
Figure 2:
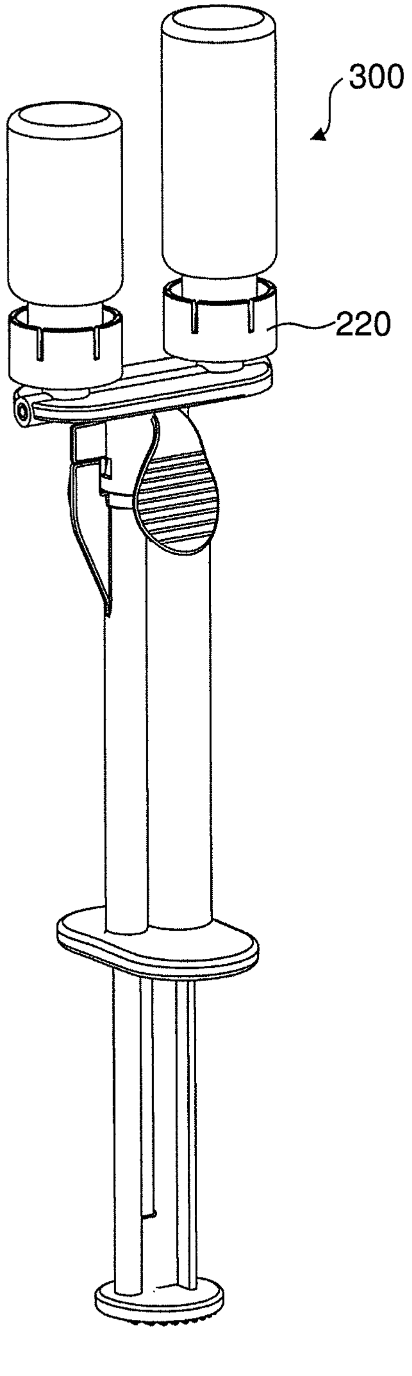
FIG. 2 shows the filling device in FIG. 1 with an inserted vial.
Figure 3:
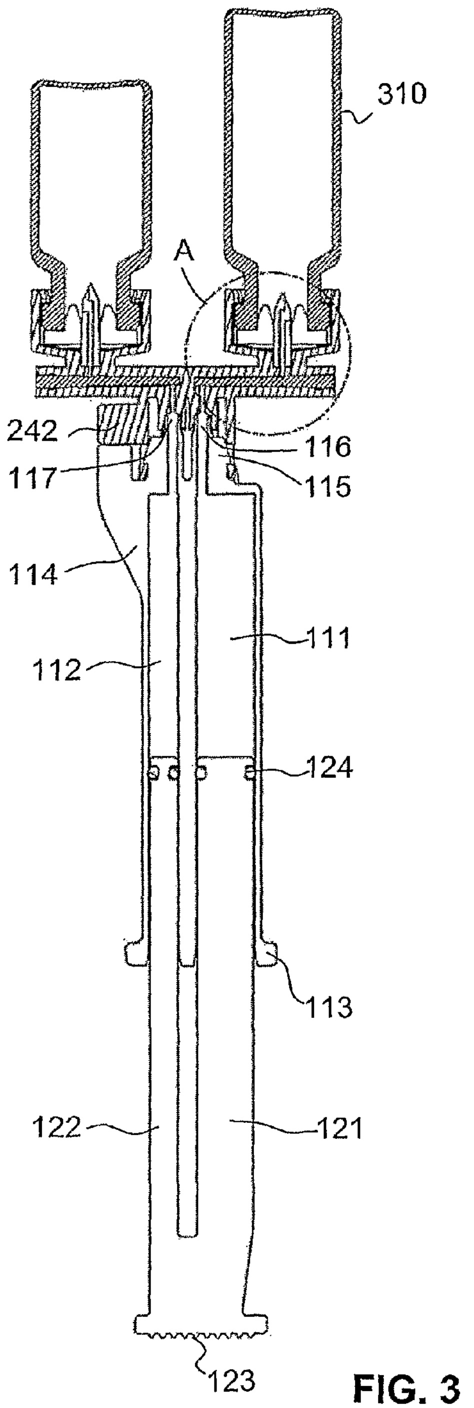
FIG. 3 shows a central longitudinal section through the filling device in FIG. 2.
Figure 4:
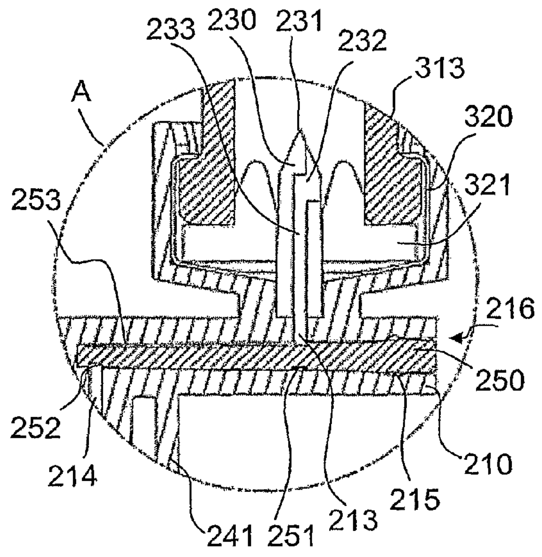
FIG. 4 shows a detailed view of area A in FIG. 3.

Along this longitudinal direction from each of the two ends of the cylindrical thickening 211 a blind-type longitudinal bore is formed, which each ends just before the middle of the thickening (FIGS. 3 and 4). Each of these bores widens slightly conically towards its open end and forms a fluid channel. The two bores are collinear to each other, i.e. they are on the same axis one behind the other.

Toward the upper side of the basic body 210 in the area of the thickening there is an inlet opening 213 for each of the bores (FIG. 4). This inlet opening 213 connects the relevant bore to a beaker-like container holder 220. The container holder 220 has a circumferential cylindrical jacket wall, which from its upper edge has multiple slits so that each section of the jacket wall interrupted by a slit forms a spring arm. On the free ends of these sections acting as spring arms retaining lugs project inwards in order to hold a container 300 in a removal position on the container holder.

The containers 300 are in the form of so-called vials with a septum seal. Each container comprises a container body 310 which is preferably made of glass, but can also be made of special plastic. Adjoining a flat bottom 311 is a circumferential cylindrical jacket wall 312 which close to the end away from the bottom has a tapered section 313. Adjoining this tapered section the jacket wall widens slightly again and defines a container opening. The appurtenant seal 320 comprises a septum 321 (a self-sealing membrane that can be punctured, see FIG. 4), which is held on the container opening by a crimped metal covering which leaves a central part of the septum free.

In order to puncture the septum 321, a puncturing element 230 of relatively hard plastic and terminating in a tip 231 at its upper end is inserted into the inlet opening 213. Laterally on the tip 231 there is a removal opening 232 which is connected to a central removal channel 233 which in turn opens into the inlet opening 213 of the basic body 210.

In the area of the closed end of each longitudinal bore in the basic body 210 there is an outlet opening 214 leading to an applicator connector 240. In the present example the applicator connector 240 is formed in one piece with the basic body 210, but can also be separate from the basic body 210 and connected to the basic body 210 in a suitable manner, e.g. through adhesion or welded.

A double-syringe-like applicator 100 can be connected and detachably fastened to the applicator connector. The applicator has an applicator body 110 with two cylindrical, parallel, proximally open reservoirs 111, 112 of the same or (in this case) different volume. At their distal ends the reservoirs open into outlets 116, 117. A plunger 121, 122 is inserted into the open proximal ends of the reservoirs. The two plungers are connected to each other at their proximal ends to form a plunger unit. In this area an operating surface 123 for the thumb of an operator is provided. A holding flange 113 is for holding the applicator between the index finger and middle finger. To this extent the applicator can be used like a commercial double syringe.

Functionally the connection between the applicator 100 and the filling device 200 essentially corresponds with the connection between a syringe/cartridge and an accessory described in WO 2007/109915. More particularly, the applicator 100 and the filling device 200 have retention means designed in accordance with this document. Specifically the applicator connector is designed as follows: each of the outlet openings 214 of the two fluid channels opens into a conically widening insert area for the outlets 116, 117 of the applicator. These outlets are designed to complement the insert area and can be inserted into these insert areas. In order to hold the applicator 100 securely on the filling device 200 the applicator has on two opposite sides, close to its distal end, adjacent to the outlets, two webs with catches 115. The applicator connector 240 has a cylindrical holding area 241 which surrounds the insert areas and the webs with the catches and on which two opposite snap-in openings are formed. The catches 115 click into the snap-in openings of the holder area 241 when the applicator is inserted.

In order to release the applicator 100 from the filling device 200, the holder area 241 is so elastically deformable that the snap connection between the catches 115 and the corresponding snap-in openings can be released through pressing on a wall area of the holder area 241 offset from the snap-in openings by approximately 90 degrees in relation to the cylinder axis of the holder area. Through such pressure the holder area 241 is deformed in such a way that the snap-in openings are pressed away radially outwards from the catches 115 and are therefore no longer in engagement with the catches. For further details and further possible embodiments of the connection between the applicator and the filling device reference is made to the already mentioned WO 2007/109915, the content of which is included herein through reference.

In order to be able to exert this pressure specifically and simply, two press wings 243 are formed on the carrier plate 212. The lateral compression of the two press wings 243 is transmitted to the snap-in openings on the cylindrical holder area 241 of the applicator connector 240 and thereby results in the release of the snap-type connection between the applicator 100 and filling device 200.

A coding wing 114 on the applicator 100 and a corresponding coding wing 242 on the filling device 200 show the correct orientation of the applicator 100 when connecting it to the filling device 200. In addition, the connectors themselves are different in order to ensure that the applicator 100 can only be connected to the filling device 200 correctly orientated.

Figure 5:
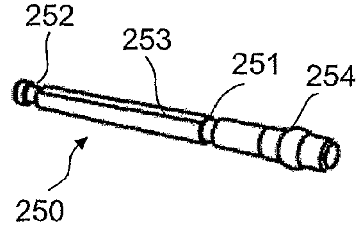
FIG. 5 shows an enlarged perspective view of an insert element.

In order to reduce the dead volume of the filling device a peg or needle-shaped insert element 250, shown only in FIG. 5, is inserted into each of the two longitudinal bores of the basic body 210. The insert element 250 serves to reduce the cross-section of the fluid channel formed by the hole between the inlet opening 213 and the outlet opening 214. For this the design of the insert element 250 essentially complements the bore in the basic body 210 and also widens slightly towards the free end of the bore so that its circumferential surface essentially adjoins the defining wall of the bore in a sealing manner. In the area of the inlet opening 213 a first annular groove 251 is provided in the circumferential surface of the insert element 250, while in the area of the outlet opening 214 a second annular groove 252 is formed. These annular grooves are connected to each other by a connecting groove running in the longitudinal direction. Together, between the inlet opening 213 and outlet opening, the annular grooves 251, 252 and the connecting grove 253 form a fluid connection jointly delimited by the grooves and the defining wall of the fluid channel. Instead of a straight connection another shape can also be selected. Alternatively or additionally, a flattened area can be provided on the circumferential surface, or the connecting grove can be replaced with a fine bore which may run, e.g., diagonally.

The insert element 250 can be simply pushed in any orientation longitudinally into the open end of the bore, the open end of the bore forming an insert opening 216 for the insert element. Because of the circumferential annular grooves 251, 252 the precise orientation of the insert element with regard to rotation of the insert element about the longitudinal axis does not matter. In order to secure the insert element 250 in the bore in the area of the insert opening it has an annular bulge 254 which engages in an annular groove 215 of the basic body 210. In this manner, further securing of the insert element 250 in the basic body 210, e.g. through adhesion or welding, can be dispensed with.

To fill the two reservoirs 111, 112 the applicator 100 is attached to the filling device 200 with plungers 121, 122 fully pressed in. The containers 300 are inserted into the corresponding container holders until they reach the removal position in which the septa of the containers 300 are punctured and the containers have engaged with the container holders. The plunger unit 120 is then retracted in order to remove the fluids from the two containers separately and simultaneously and transfer them into the reservoirs 111, 112. During this only a small quantity of each fluid is lost in the filling device. By pressing on the press wings 243 the applicator 100 is released from the filling device 200. Subsequently an accessory, e.g. a mixer or sprayer can be connected to the applicator and the fluids can be discharged from the applicator through the accessory.

Figure 6:
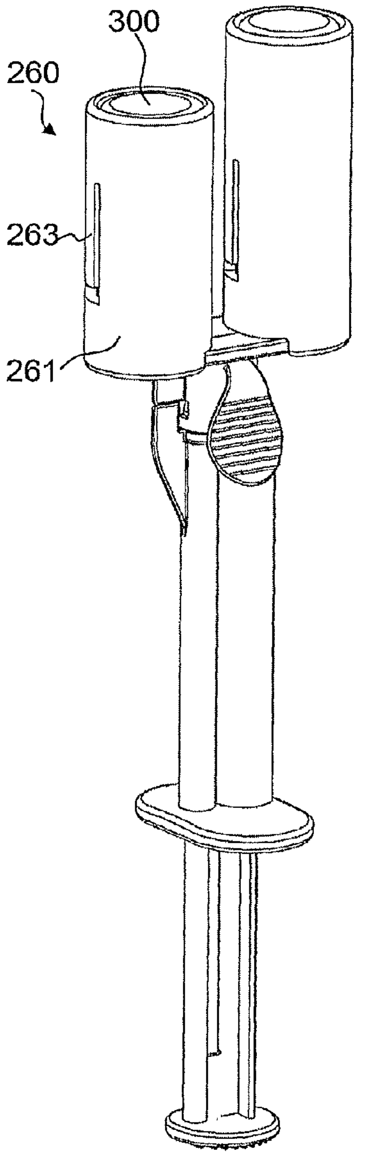
FIG. 6 shows a perspective view of a first exemplary embodiment of a filling device in accordance with the invention.
Figure 8:
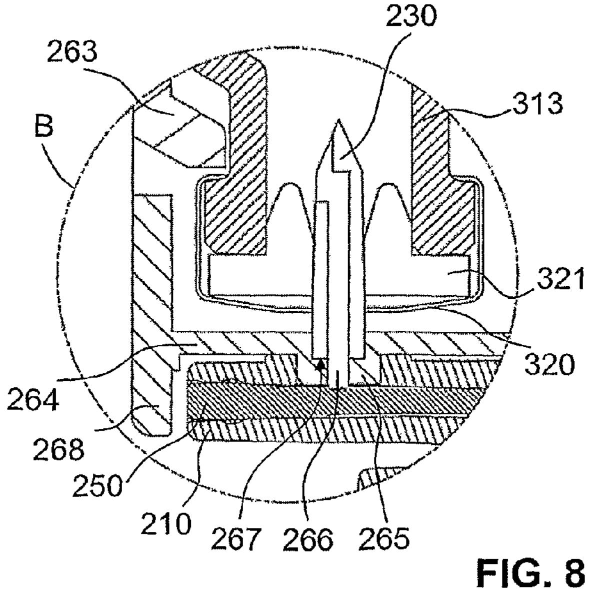
FIG. 8 shows a detailed view of area B in FIG. 7.
Figure 9:
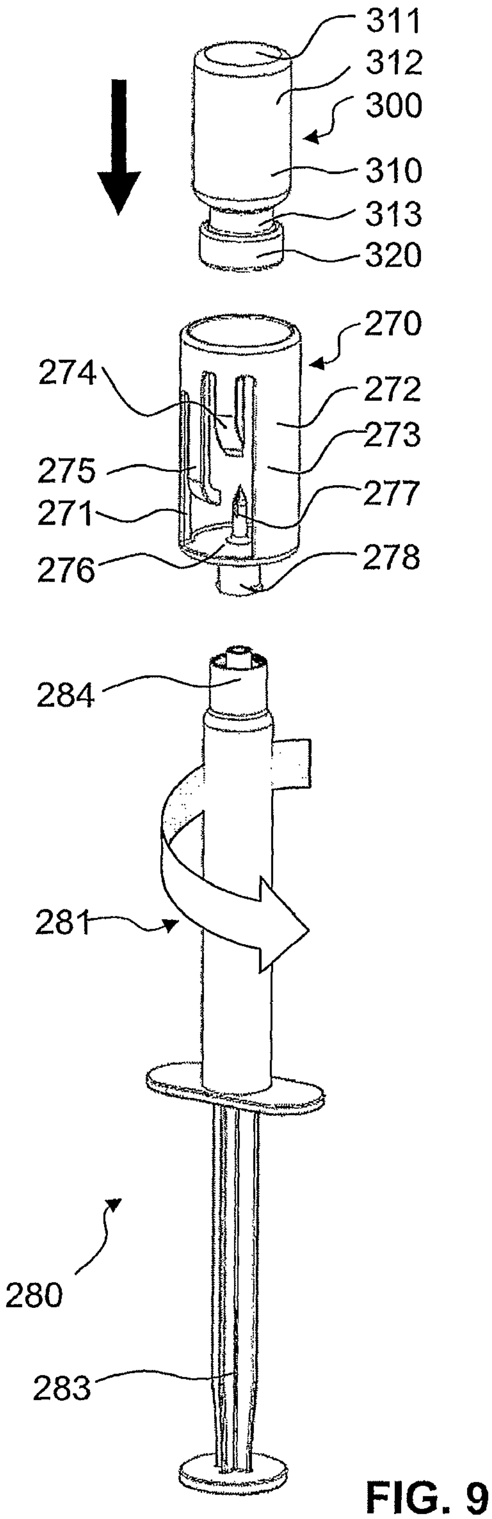
FIG. 9 shows a perspective view of a second exemplary embodiment of a filling device in accordance with the invention.

In FIGS. 6 and 8 a first embodiment of a device in accordance with the invention is shown, which is designed to remove a fluid from at least one container sealed with a closure that can be punctured. This embodiment in accordance with the invention differs from the filling device in FIGS. 1 to 5 through the design of the container holders. More particularly, the manner in which the vials are held in the container holder is different.

The container holders 260 are here chimney-like, cylindrical structures which are of sufficient length to hold the entire container in terms of length. Whereas the container holders shown FIGS. 1 to 4 were produced in one piece with the basic body 210, the container holders 260 of the embodiment in FIGS. 6 to 8 are produced separately from the basic body 210 and connected to it by way of a suitable connection, e.g. a welded connection.

Figure 7:
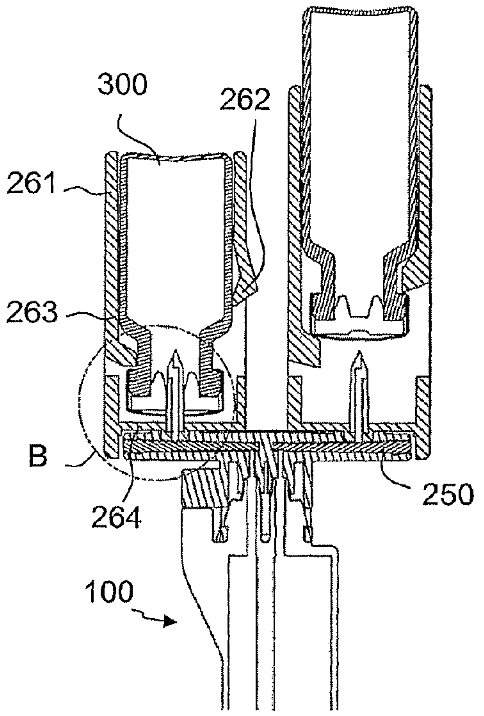
FIG. 7 shows a partial view of a central longitudinal section through the filling device in FIG. 6.

In the embodiment in FIGS. 6 to 8 each inlet opening 213 in the basic body has a larger diameter than in the filling device in FIGS. 1 to 5. The container holder 260 has a base 264 from which a peg 265 extends into the inlet opening 213. A through opening 266 through the base 264 and peg 265 forms a connection between the removal channel of the puncturing element 230 and the fluid channel in the basic body 210, the puncturing element 210 being inserted into an area of the outlet opening 266 with increased diameter and rests with its lower margin on an edge stop 267.

From the outer margin of the base 264 a cylindrical jacket wall 261 extends upwards. In addition, a partially cylindrical, apron-like cover extends downwards partially laterally surrounding the basic body 210 and, more particularly, covering the insert opening 216 for the insert element 250.

In the jacket wall 261 a catch structure 262, 263 is formed on each of two opposite sides. The first catch structure 262 is further from the basic body 210 than the second catch structure. Each of the catch structures has a spring arm, on the free end of which a catch lug is provided which extends into the interior of the container holder 260. The second catch structure 263 is arranged so that through a snap connection it fixes the container 300 in a fully inserted removal position in which the puncturing element 230 has punctured the seal 220. For this the catch lug of the second catch structure 263 engages in the tapered area 313 of the container body and thus prevents the container from being pulled out of the container holder. The first catch structure 262 fixes the container onto the container holder when the container is in a storage position in which the seal 320 is at a certain distance from the tip of the puncturing element 230. On the one hand the first structure 262 therefore prevents the container 300 from being pulled out, and on the other hand this catch structure prevents further movement of the container 300 in the direction of the puncturing element 230. In order to advance the container further in the direction of the puncturing element 230 and thereby puncture the seal, increased force must be applied. Via an oblique surface facing way from the basic body, the catch lug is pushed outwards by this increased force and releases the container for further movement.

In this way it is possible to store the containers on the filling device without the container seals being punctured or the containers falling out of the device.

In FIGS. 9 to 11*b* a second embodiment of a filling device 270 in accordance with the invention is illustrated. In this embodiment the filling device 270 has a basic body 271 with only one container holder 272 and serves to fill an applicator 280 with a fluid from a container 300. Here the applicator 280 is in the form of a single syringe which has an applicator body 281 with a reservoir 282 and plunger 283 which can be moved therein.

The container holder 272 into which here a container 300 in the form of a vial can be inserted, has a circular base 276 from which over an angle range of approximately 270° a jacket wall extends upwards. The jacket wall 273 is partially cylindrical in the section facing the base 276 and thereby defines a longitudinal axis of the filling device 270. In an end area arranged at a distance from the base 276 the jacket wall 273 is however circumferentially designed, i.e. cylindrically. The jacket wall 273 thus has an essentially rectangular window opening which is defined at the bottom by the base 276 and at the top by the cylindrical section of the jacket wall 273. In the longitudinal direction the length of the jacket wall 273 approximately corresponds with the total length of the container 300.

Within the window opening of the jacket wall 273 there are two catch structures 274 and 275 which are arranged offset with regard to each other in the circumferential direction of the jacket wall. The two catch structures 274 and 275 are each designed as spring arms which extend downwards in a longitudinal and parallel manner from the circumferentially designed end area of the jacket wall 273. Compared with the spring arm of catch structure 274, the spring arm of the catch structure 275 extends further towards the base and is longer in the longitudinal direction. Both spring arms are also slightly flexible in the radial direction. In an alternative embodiment the two catch structures could be arranged diametrically opposite each other instead of next to each other to take up as little space while retaining as much stability of the container holder as possible.

At the free ends of the spring arms of the catch structure 274, 275 catch lugs extend radially inwards. The catch lugs are slightly inclined downwards towards the base 276. In particular they have an oblique surface, the surface normal of which essential points away from the base 276 in the longitudinal direction and is slightly inclined with regard to the longitudinal axis.

The base 276 has a central through opening which opens upwards into a hollow needle-like puncturing element 277 which projects into the container holder 272. Downwards the central through opening opens into an applicator connector 278 which is arranged on the side of the base 276 opposite the puncturing element 277. Through the applicator connector 278, puncturing element 277 and the base 276 a continuous fluid channel 279 is thus formed. The applicator connector 278 is for connecting an applicator 280 and is here in the form of a Luer connection with a female Luer cone and locking structure arranged around it.

Figures 10A, 10B, 10C:
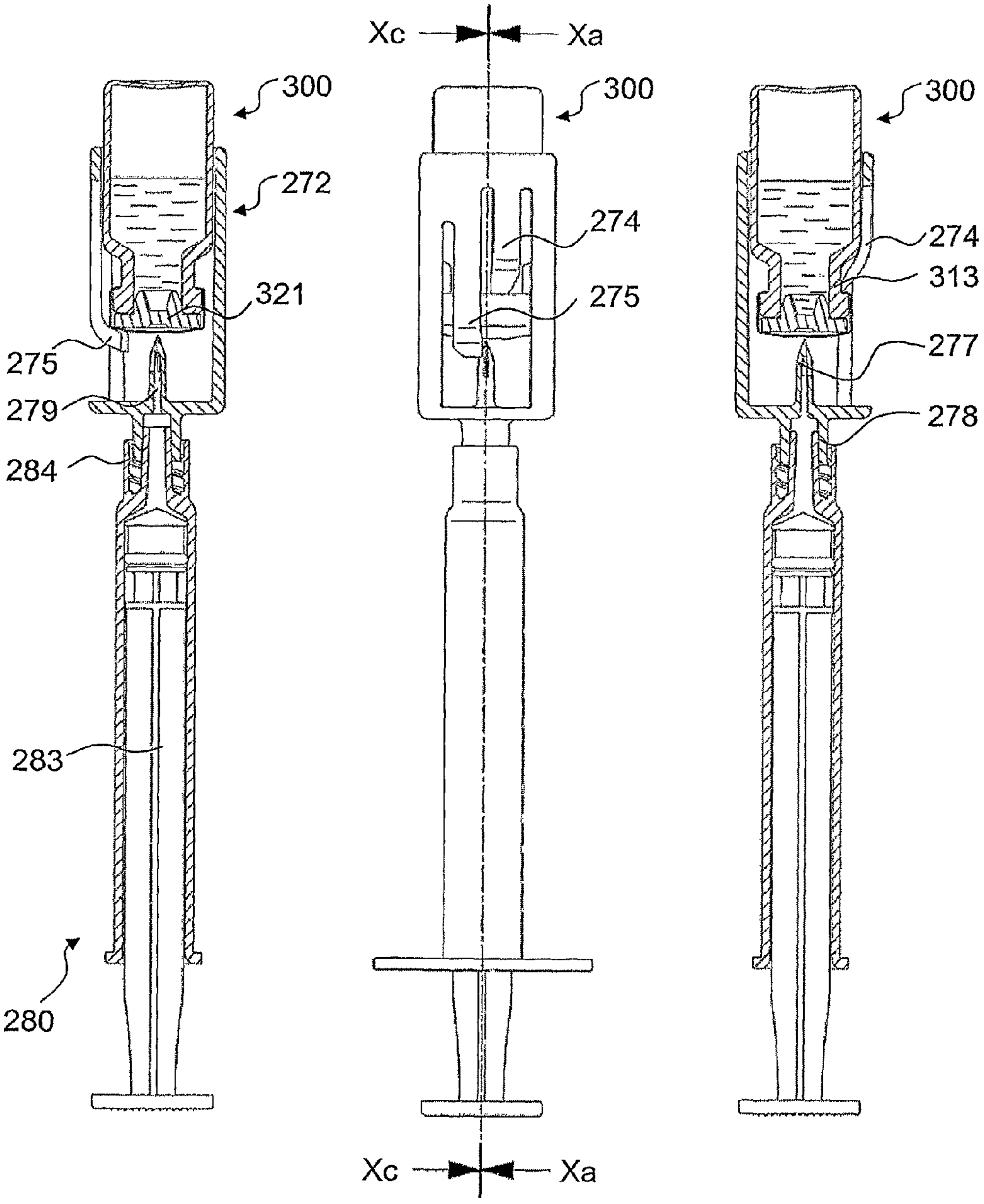
FIG. 10*a* shows a first central cross-sectional view in plane Xa-Xa though the filling device in FIG. 9 in the storage position.
FIG. 10*b* shows a side view through the filling device in FIG. 9 in the storage position.
FIG. 10*c* shows a second cross-sectional view in plane Xc-Xc though the filling device in FIG. 9 in the storage position.

In FIGS. 10*a* to 10*c* a container 300 is inserted from above (arrow direction in FIG. 9) into the container holder 272 of the filling device 270. In doing so, in the longitudinal direction the closure 320 of the container 300 comes into contact with the catch lug of the second catch structure 275. The septum 321 is in the vicinity of the puncturing element 277, but still at a distance from it. Further advancing of the container 300 toward the puncturing element 277 is prevented by the second catch structure 275. The second catch structure 275 thus secures the container 300 from further insertion into the container holder 272. This prevents unintentional puncturing of the septum 321 by the puncturing element 277. At the same time the first catch structure 274 projects into the tapered section 313 of the container 300 in such a way that it prevents a movement of the container 300 away from the puncturing element 277 and out of the container holder 272. As the catch lug of the first catch structure 274 is inclined towards the base 276 forcibly pulling the container 300 out of the container holder 272 would result in irreversible destruction of the first catch structure 274. The first catch structure 274 thus fixes the container 300, which is snapped in between the first and the second catch structure, in the container holder 272. The container 300 is in a storage position and can thus be stored, marketed or sold together with the filling device 270. As the container 300 is surrounded by the jacket wall 273 it is optimally protected. When sold the applicator 280 can already be connected to the applicator connector 278 by means of a Luer connection 284.

Figure 11A:
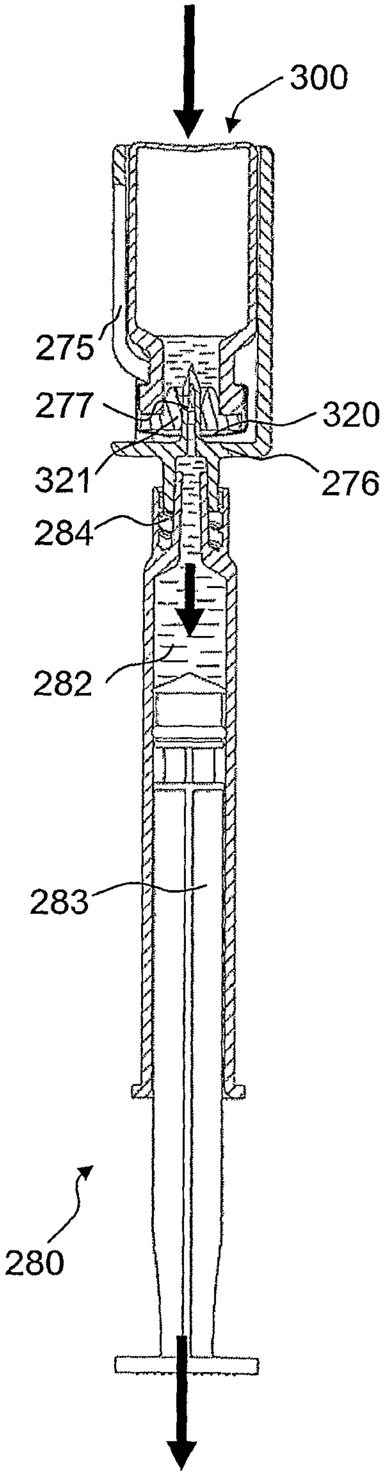
FIG. 11*a* shows a central cross-sectional view in plane XIa-XIa though the filling device in FIG. 9 in the removal position.
Figure 11B:
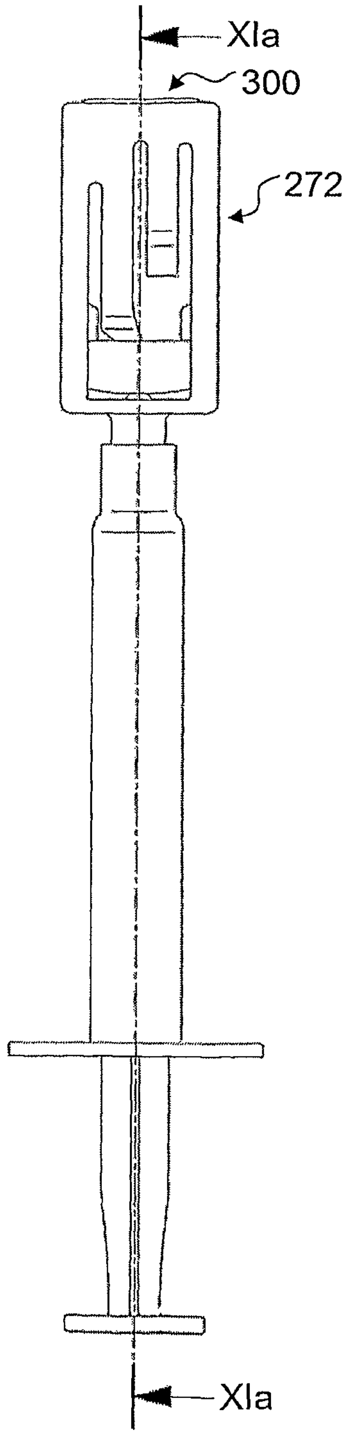
FIG. 11*b* shows a side view through the filling device in FIG. 9 in the removal position.

To fill the applicator the user presses the container 300 out of this storage position using increased force further in the direction of the puncturing element 277. The two spring arms of the catch structures 274 and 275 are thereby pressed radially outwards due to the oblique surfaces of their catch lugs as a result of which the container 300 can be moved along the longitudinal axis (or in the direction of the arrow in FIG. 11*a*) up to the stop of the closure 320. During the forward movement the puncturing element 277 punctures the septum 321 of the container 300 so that a fluid connection is created between the interior of the container 300 and the reservoir 282 of the applicator 280. Once the container closure 320 has been advanced to the base 276, the catch lug of the second catch structure 275 snaps into the tapered section 313 of the container 300. The container 300 is thus fixed in a position relative to the filling device 270 and is in the removal position, which is shown in FIGS. 11*a* and 11*b*. The substance stored in the container 300 can be transferred into the applicator 280 by retracting the plunger 283 from the applicator body 281 (direction of the arrow in FIG. 11*a*). The second catch structure 275 prevents the container 300 being removed from the container holder 272.

In this exemplary embodiment the filling device 270 is produced in one piece of a plastic material by way of injection moulding.

A number of further variations are of course possible. The container holder can be designed in a different way from the manner illustrated here. More particularly, it is conceivable for a single container holder to hold two containers jointly, e.g. in the form of a common hood for two containers. It is also conceivable for the container(s) to be held in a holding structure and the holding structure with the containers inserted therein to be inserted complete into the corresponding container holder as is the case in some embodiment of already cited U.S. Pat. No. 6,488,650. It is of course also conceivable that interlocking does not take place directly between the container holder and the container, but between the container holder and the inserted holding structure.

Instead of an applicator of the type set out here other types of applicators can of course be used, more particularly applicators as illustrated in WO 2009/144085 or WO 2007/109915. Conventional double syringes, or single syringes combined into unit can also be used. Accordingly it is also possible to design the applicator connector differently.

A filling device of this type can also be used for filling other types of reservoirs from containers with a seal that can be punctured. It is conceivable in particular to use carpules (containers with septum seal and moveable plunger) in place of the vials illustrated above. In this, instead of an applicator another type of accessory can be connected, e.g. a mixer to mix the contents of two carpules.

A number of further variations are possible and the invention is not restricted in any way to the examples of embodiment described above.

The invention claimed is:

1. A device for removing a fluid from at least one container sealed with a closure that can be punctured, the device comprising:

a basic body having an inlet opening and an outlet opening which are connected by a fluid channel;

a hollow needle-like puncturing element for puncturing the closure of the container in a removal position, the puncturing element being connected with the inlet opening and terminating in a tip, such that the puncturing element extends along a first direction from the inlet opening to the tip; and a container holder having a jacket wall and being connected to the basic body for holding the container on the device, the jacket wall having a cylindrical shape with a circumferential surface extending from the basic body along the first direction, the container holder having a first catch structure for fixing the container by means of a releasable snap connection on to the container holder in a storage position in which the container is further from the basic body than in the removal position, the container holder having a second catch structure for fixing the container in the removal position on the container holder by means of the snap connection, and the first catch structure and the second catch structure each having a spring arm with a free end at which a catch lug extending into the jacket wall is formed, each spring arm being formed in the jacket wall and extending in the region of the circumferential surface along a second direction towards its free end, the second direction being oriented opposite to the first direction, wherein the first catch structure is adapted to prevent further movement of the container in the direction of the puncturing element in such a way that an increased force must be applied to puncture closure and break the seal provided by the closure, and wherein the container is snapped in between the first catch structure and the second catch structure while in the storage position.

2. The device in accordance with claim 1, wherein the first catch structure and the second catch structure are arranged diametrically opposite each other in relation to the circumferential direction of the jacket wall.

3. The device in accordance with claim 1, wherein the first catch structure and the second catch structure are arranged directly next to one another in relation to a circumferential direction of the jacket wall.

4. The device in accordance with claim 1, wherein the first catch structure and the second catch structure each have oblique surfaces, the surface normal of which points away from the inlet opening of the basic body while being inclined with regard to a longitudinal axis along which the container can be moved from the storage position into the removal position.

5. The device in accordance with claim 1, wherein the container holder has a base from which a peg extends into the inlet opening of the basic body, wherein an through opening is formed through the peg and the base, and wherein the puncturing element is held in the through opening.

6. The device in accordance with claim 1, the device being configured for filling at least one reservoir of an applicator, the device having an applicator connector for connecting the reservoir of the applicator with the outlet opening.

7. The device in accordance with claim 6, wherein the container holder has a base from which the puncturing element and the applicator connector extend in opposite directions.

8. The device in accordance with claim 6, wherein the applicator connector is made in one piece with the basic body.

9. The device in accordance with claim 1, wherein the device has two or more puncturing elements and just as many container holders in order to hold two or more containers on the device, and wherein each of these container holders has a first catch structure.

10. The device in accordance with claim 1, wherein the jacket wall has a circumferentially designed end area, and wherein the two spring arms of the first and of the second catch structure each extend from the circumferentially designed end area of the jacket wall to the basic body.

11. The device in accordance with claim 1, wherein the second catch structure prevents the container from being pulled out of the container holder in the removal position.

12. The device in accordance with claim 11, wherein the container comprises a container body with a tapered area, and wherein the catch lug of the second catch structure is adapted for engaging in this tapered area, in order to prevent the container from being pulled out of the container holder in the removal position.

13. The device in accordance with claim 1, wherein the first catch structure prevents the container from being pulled out of the container holder in the storage position and secures the container from further insertion into the container holder.

14. The device in accordance with claim 1, wherein the container comprises a container body with a tapered area, and wherein the catch lug of the first catch structure is adapted for engaging in this tapered area, in order to prevent the container from being pulled out of the container holder in the storage position.

* * * * *